United States Patent [19]

Mills

[11] Patent Number: 5,372,535
[45] Date of Patent: Dec. 13, 1994

[54] LEAFCUTTER BEE MANAGEMENT SYSTEM INCLUDING A LAMINATE BEE BOARD

[76] Inventor: Jerry Mills, 144 S. Slope, Emmett, Id. 83617

[21] Appl. No.: 188,026

[22] Filed: Jan. 28, 1994

[51] Int. Cl.⁵ .............................................. A01K 47/00
[52] U.S. Cl. .............................................. 499/4; 449/36
[58] Field of Search .................... 449/4, 36, 56

[56] References Cited

U.S. PATENT DOCUMENTS

| | | | |
|---|---|---|---|
| 502,486 | 8/1893 | Dewey | 449/36 |
| 3,191,199 | 6/1965 | Barnes, Jr. | 449/4 |
| 3,267,497 | 8/1966 | Dority | 449/4 |
| 3,936,894 | 2/1976 | Barber | 449/4 |
| 4,319,371 | 3/1982 | Weiderrich | 449/4 |
| 4,628,558 | 12/1986 | Pederson | 449/4 |
| 4,765,007 | 8/1988 | McCarthy | 449/4 |
| 4,787,108 | 11/1988 | Norman | 449/1 |

OTHER PUBLICATIONS

University of Idaho College of Agriculture Cooperative Extension System, Bulletin No. 538, *Alfalfa Leafcutting Bee Management in Idaho*.

*Primary Examiner*—Robert P. Swiatek
*Attorney, Agent, or Firm*—Frank J. Dykas; Craig M. Korfanta

[57] ABSTRACT

A bee nest made from a plurality of bee board laminates held in close side by side relation by a permanent, flexible and lightproof backing material. The nest includes a closure for releasably opening and closing the nest at the front edges of the laminates.

4 Claims, 5 Drawing Sheets

LEAFCUTTER BEE MANAGEMENT SYSTEM INCLUDING A LAMINATE BEE BOARD

DESCRIPTION

1. Technical Field

This invention relates generally to management systems and nests for leafcutter bees, and specifically to a laminate bee board with a flexible permanent backing to facilitate handling and management.

2. Background

Management of leafcutter bees for pollenization of alfalfa crops has had a significant effect on the commercial success of the alfalfa seed industry. The leafcutter bee is managed to time its life cycle to coincide with the alfalfa crop management cycle. The leafcutter bees are used to pollinate the alfalfa blossoms. A blossom appears on the alfalfa plants approximately 45 days after the alfalfa hay has been "set back", usually by mowing, swathing or roto-beating.

The life cycle of the bee is managed through temperature control of its environment. After the mature bees emerge, the females begin to nest within 2-3 days. The females always nest in existing tunnels. The female bee chews a piece of a leaf out of plants in the immediate area of the nest. The bee then puts the piece of leaf in the tunnel to form a cup. Next, she fills the cup with a nectar and pollen mixture, lays an egg and then caps the cup with another piece of leaf, forming a cell. She repeats these steps until the tunnel is filled with cells.

The incubation of the egg is also managed. The egg hatches into a larva, which eats the nectar and spins a cocoon. The cocoon normally remains dormant for the winter. A mature bee will emerge from the cocoon in response to a specific warm temperature range. This emergence is again timed to coincide with the blossoming of the alfalfa. This management cycle is repeated.

With the growth of the industry of raising pollinators, certain management problems have become significant. Leafcutter bees are susceptible to predators and certain diseases, the most significant of which is called chalkbrood. Chalkbrood can cause up to a 50% mortality to the bee larvae. This disease has increased in prevalence in recent years. Various predator insects and parasites also have a significant effect on the production of leafcutter bees.

In response to these management problems the industry has instituted a number of management practices. The use of laminated nesting materials, specifically wood laminates, provide superior predator and parasite prevention along with a natural attraction for the bees. However, laminate bee boards tend to be expensive and require more handling in assembling and disassembling them for cell removal, cleaning and sterilization. Consequently, synthetic bee board materials, such as solid polystyrene blocks, have experienced a rise in popularity. These solid bee boards lend themselves to automated cell removal, cleaning and sterilization. They are, however, prone to predator infestation and tampering by other animals. Additionally, the bees are not naturally attracted to the synthetic material for nesting.

Current sterilization techniques involve removing the cells from the bee nest, dipping the cells in a sterilizing solution such as a chlorine solution and air drying the cells. Cleaning and sterilization of the nests is done separately.

Problems with the current management techniques include the necessity of carrying out the sterilization in multiple steps, using multiple machines and a relatively intensive labor input, especially with laminate type bee boards. Additionally, if not performed carefully contamination can be spread instead of inhibited. The laminates can be difficult to handle and assemble and disassemble for the sterilization procedures. A more thorough discussion representative of current management options and practices and their associated advantages and disadvantages is contained in Bulletin No. 538, from Cooperative Extension System, University of Idaho, College of Agriculture, "Alfalfa Leafcutting Bee Management In Idaho" incorporated by reference herein.

What is needed is simpler effective tool for management of leafcutter bees to help prevent disease and inhibit predators.

It is an object of the present invention to provide a laminate nest which takes advantage of the inherent predator resistance of laminate nests, yet which is simple to manage, clean and sterilize.

It is a further object of the present invention to provide a laminate nest that requires less steps and less management when processed during nest management.

DISCLOSURE OF INVENTION

The present invention provides a bee nest made from a plurality of bee board laminates held in close side by side relation by a permanent, flexible and lightproof backing material. The nest includes a means for releasably opening and closing the nest at the front edges of the laminates. Each laminate has a front edge, back edge and two side edges bounding two generally planar surfaces. The planar surfaces have closely parallel spaced elongated grooves formed therein extending between the front and back edges. The grooves are aligned to form tunnels in the nest when the laminates are oriented in close, parallel juxtaposition to each other.

The flexible, lightproof binding is permanently attached to the back edge of the laminates. The attachment of the binding allows the laminates to be adjustably oriented between a closed position, having the laminates in a side by side orientation, and an open position with the planar surface of two adjacent laminates positioned to form one continuous planar surface of grooves, for cleaning and sterilization management. The closed position has the grooves of the laminates forming the tunnels of the nest. The binding maintains the correct orientation of the laminates, while simultaneously allowing the laminates to be manipulated and positioned for management and returned to the desired orientation with a minimum of labor and handling.

BEST MODE FOR CARRYING OUT INVENTION

Figure 1:
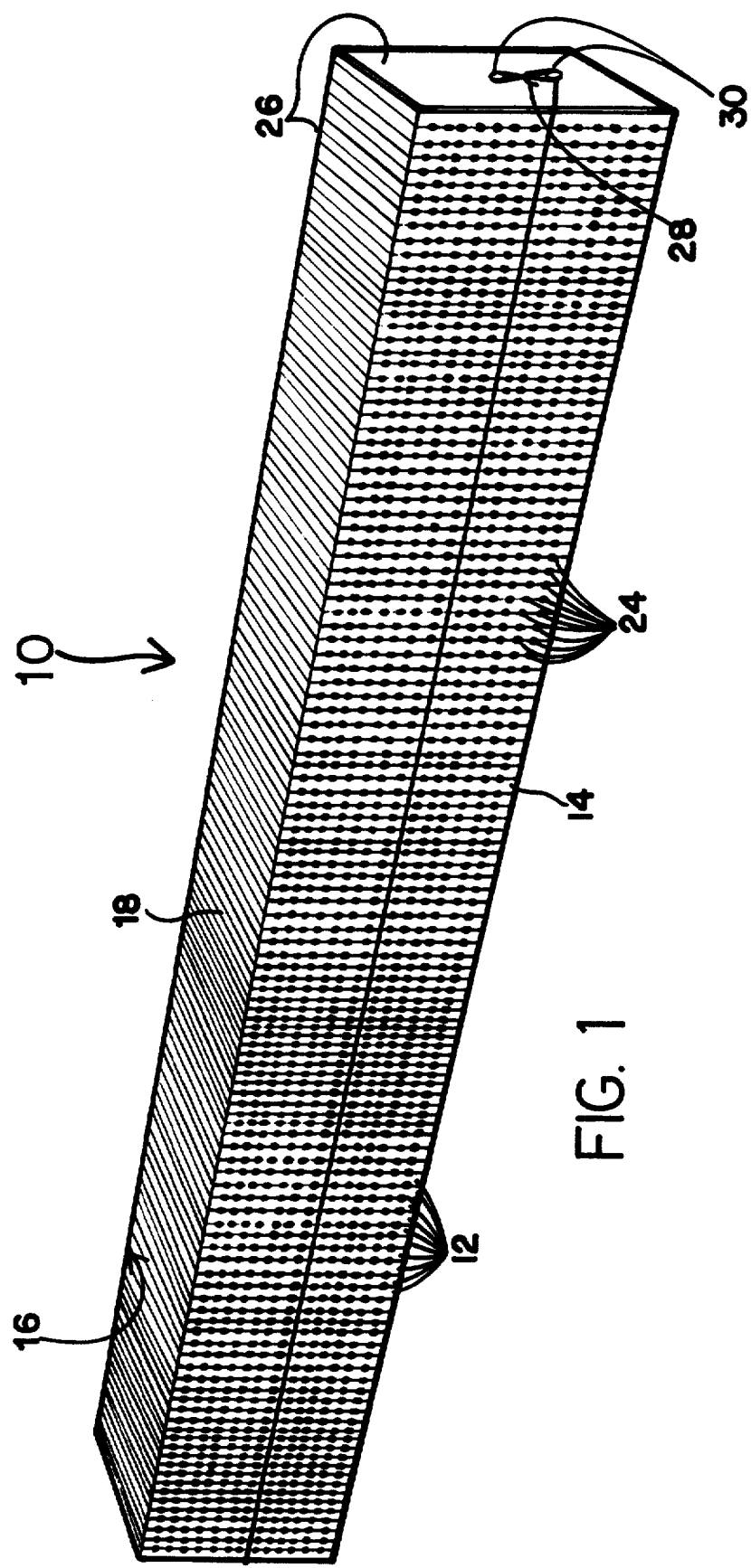
FIG. 1 is a front perspective view of the present invention.

Referring now to FIGS. 1–5, nest 10 generally is made up of a plurality of laminates 12 positioned in close side by side relation and permanently bound at their back edges 16 to flexible backing 26 and held in this closed position by fastener 28 and cleat 30.

Figure 2:
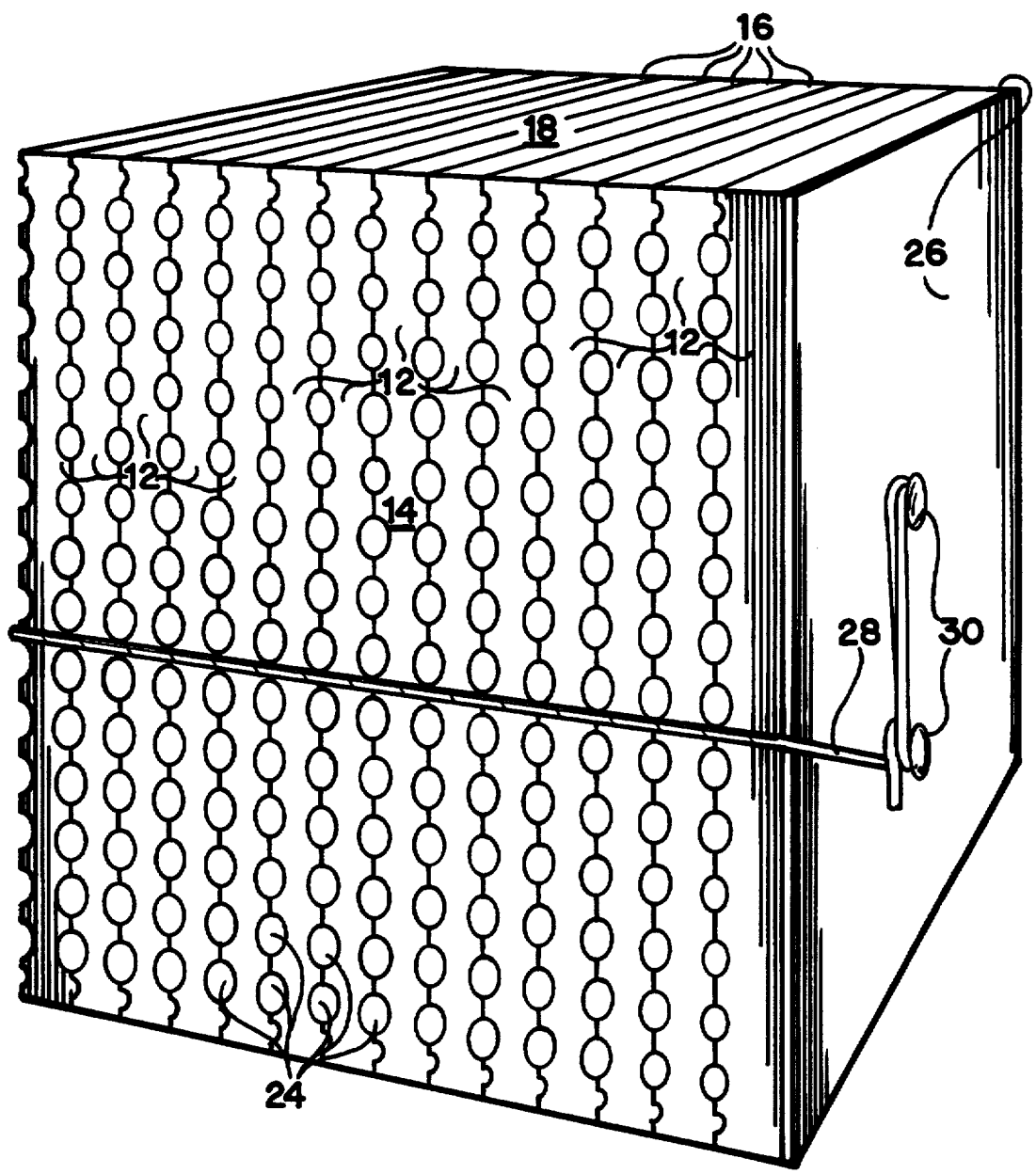
FIG. 2 is an detailed front perspective view of the present invention.
Figure 3:
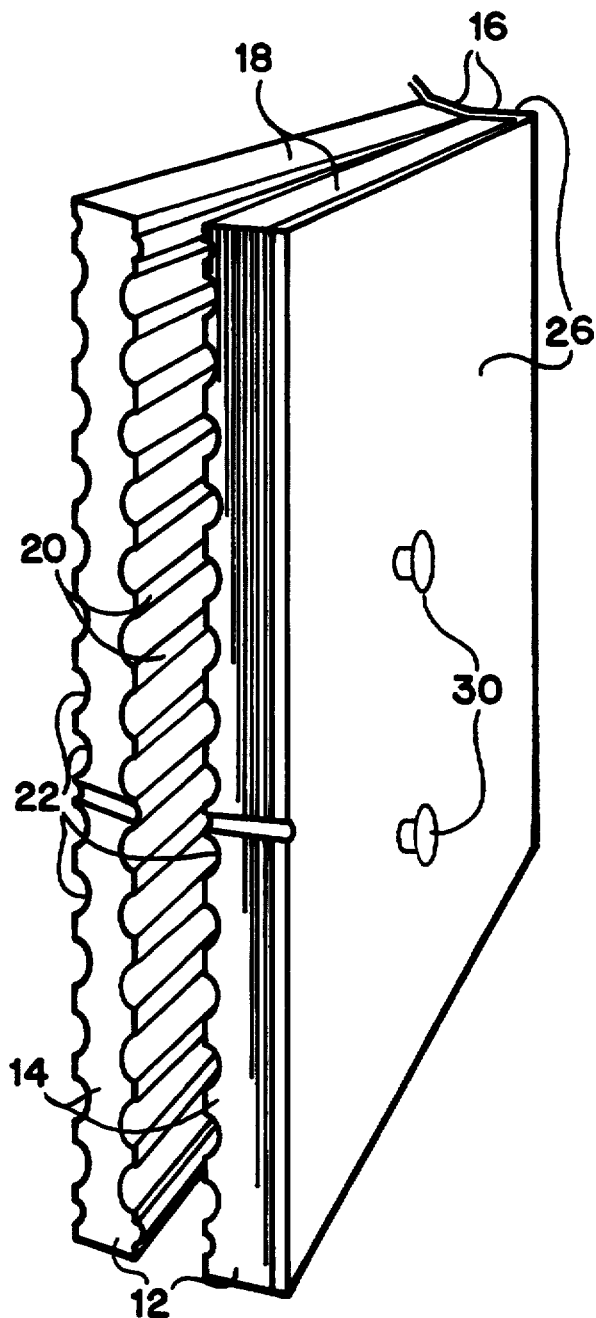
FIG. 3 is a second detailed front perspective view of the present invention.

Each laminate 12 is generally rectangular in shape with a perimeter defined by front edge 14, back edge 16 and side edges 18. Each laminate 12 has two planar surfaces 20, which in turn each have closely parallel spaced grooves 22 formed therein. Grooves 22 are shaped and positioned to form tunnels 24 when a plurality of laminates 12 are placed in close juxtaposition, as seen in FIGS. 2 and 3. Preferably, laminates 12 are formed out of wood, but they could also be formed out of polystyrene, for example, or any other suitable material.

Binding 26 permanently attaches to back edge 16 of each laminate 12 and also covers outer planar surface 20 on the endmost laminates 12 on each end of nest 10 to define the overall length of nest 10. Binding 26 is made from a flexible and lightproof material. In the preferred embodiment, binding 26 is a dark colored vinyl, such as PVC fabric, but binding 26 can be formed from any appropriate material that is durable, light proof and flexible.

Fastener 28 is attached to binding 26 on one outside surface of endmost laminate 12. Cleat 30 is attached to binding 26 on the outside surface of the opposite endmost laminate 12. In the preferred embodiment fastener 28 is a cord, but fastener 28 can be any reclosable device including a strap and buckle, velcro, small gauge chain and hook or strap with a snap closure. In the preferred embodiment cleat 30 is formed by a pair of raised small metal discs or washers for anchoring fastener 28. Cleat 30 may also be any appropriate device or structure or device that works in cooperation with fastener 28 to allow nest 10 to be releasably closed.

Figure 4:
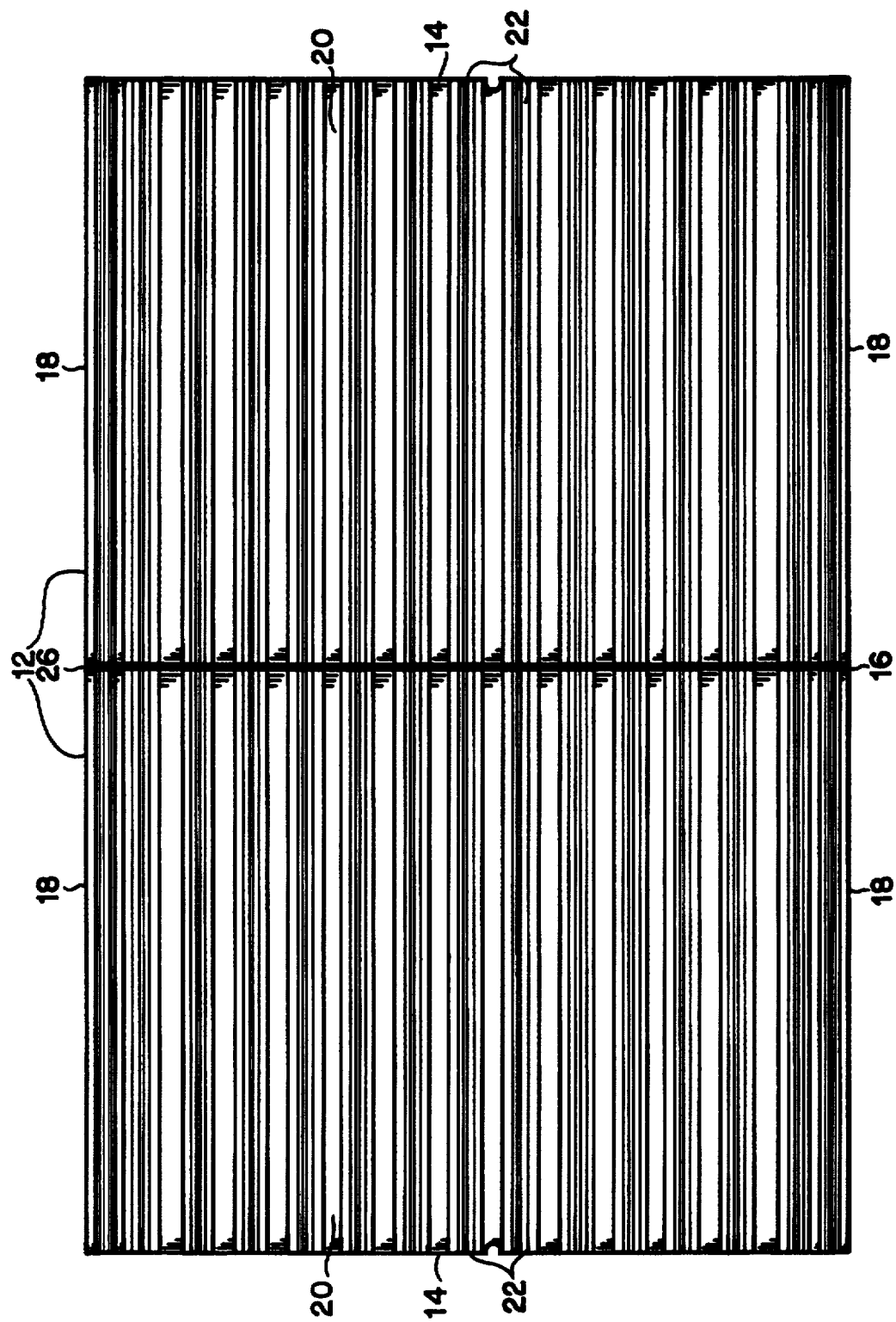
FIG. 4 is a end view showing the invention in an open position with the planar surface of two adjacent laminates positioned to form one continuous planar surface of grooves.

In practice, a plurality of boards of laminate 12 are permanently attached by back edge 16 to binding 26 to obtain nest 10 of desired dimensions depending on the individual management system in place. Each laminate 12 is oriented so that grooves 22 form tunnels 24 when two laminates 12 are juxtapositioned. Additionally, binding 26 is flexible enough to allow any two sequential boards of laminate 12 to be opened with back edge 16 of both boards of laminate 10 in juxtaposition, as best seen in FIG. 4, such that planar surfaces 20 of both boards form one continuous surface, to allow improved cleaning and sterilization of tunnels 24 and surfaces 20.

Cleaning and sterilization management can be automated and reduced to a single step system. In the single-step system two sequential boards of laminate 12 are opened such that planar surfaces 20 of both boards form one continuous surface and the "pencils" of cells or cocoons are pushed out. The pencils are pushed into a tumbler which functions to break up the pencils into loose cells and simultaneously wash and sterilized the cells. The sterilized loose cells are moved to drying trays and are ready for dormant storage after drying. The continuous surface formed by planar surface 20 of two sequential boards of laminate 12 is scrubbed and sterilized in the same step as pencil removal. Nest 10 is manipulated through the automated process in a stepped manner that allows the one-step system to be performed on one pair of sequential planar surfaces 20 and repeated on the next sequential pair of planar surfaces 20, until all planar surfaces 20 of nest 10 have been processed.

Figure 5:
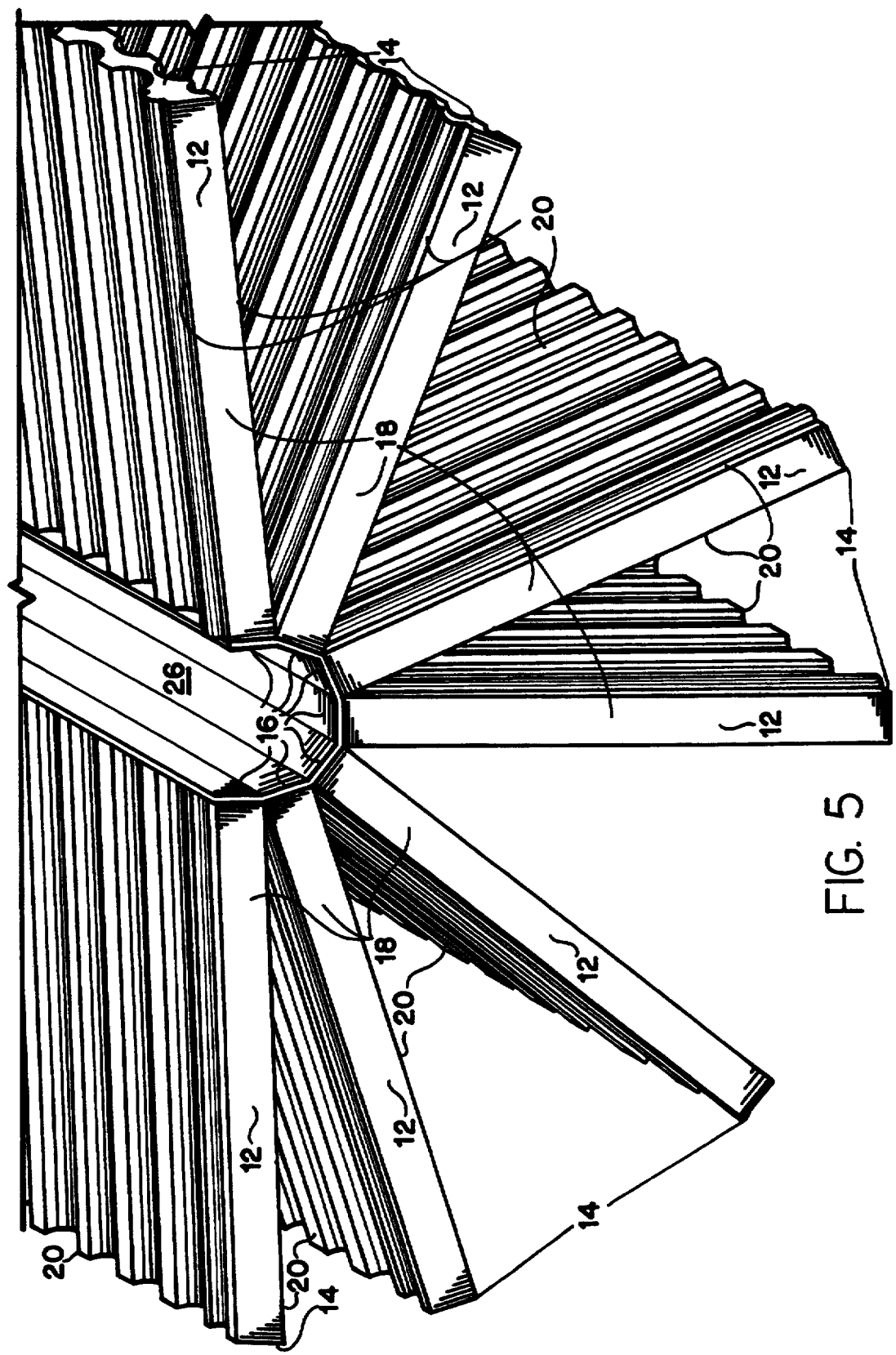
FIG. 5 is a top isometric view of the present invention.

Binding 26 keeps laminates 12 in alignment in both the open position for cleaning as seen in FIGS. 3 and 5 and the closed position, as seen in FIGS. 1 and 2, when tunnels 24 of nest 10 are occupied. This greatly reduces the labor and decreased the handling required in the management of nest 10.

While there is shown and described the present preferred embodiment of the invention, it is to be distinctly understood that this invention is not limited thereto but may be variously embodied to practice within the scope of the following claims.

I claim:

1. A permanently backed nest for bees comprising:
   a plurality of bee board laminates, each laminate being generally rectangular and having two planar surfaces bounded by a front edge, a back edge, and two side edges, the planar surfaces having a plurality of spaced, parallel grooves formed therein and extending between the front and back edges, the grooves being positioned to form a series of closely spaced, edge bound tunnels by any two contiguous laminates; and
   a lightproof flexible binding permanently attached to the back edges of the laminates, the laminates being juxtaposed one to another with the binding extending across the plurality of laminates.

2. The permanently backed nest for bees of claim 1 further comprising a releasable means for securing the bound laminates in tight parallel juxtaposition.

3. The permanently backed nest for bees of claim 2 wherein the flexible binding is configured to permit the laminates to be aligned in a continuous series of orientations ranging from an "open" orientation with the bound edge of any two laminates in contact and their planar surfaces aligned such that the two boards form one continuous planar surface, to a "closed" orientation having the laminates in tight parallel juxtaposition and the grooves of any two contiguous laminates forming a series of closely spaced, edge bound tunnels.

4. The permanently backed nest for bees of claim 1 wherein the flexible binding is configured to permit the laminates to be aligned in a continuous series of orientations ranging from an "open" orientation with the bound edge of any two laminates in contact and their planar surfaces aligned such that the two boards form one continuous planar surface, to a "closed" orientation having the laminates in tight parallel juxtaposition and the grooves of any two contiguous laminates forming a series of closely spaced, edge bound tunnels.

* * * * *